United States Patent [19]

Cross

[11] Patent Number: 4,863,772

[45] Date of Patent: Sep. 5, 1989

[54] LABEL STOCK WITH DRY SEPARATION INTERFACE

[75] Inventor: Patricia Cross, Chesterland, Ohio

[73] Assignee: Avery International Corporation, Painesville, Ohio

[21] Appl. No.: 185,349

[22] Filed: Apr. 20, 1988

Related U.S. Application Data

[63] Continuation of Ser. No. 801,759, Nov. 26, 1985, abandoned.

[51] Int. Cl.[4] .......................... A61F 13/02; C09J 7/02; B32B 31/00

[52] U.S. Cl. ...................................... 428/40; 428/354; 156/242; 156/248

[58] Field of Search ...................... 428/40, 41, 42, 202, 428/343, 352, 354, 914; 156/230, 240, 246, 247, 248, 249, 289, 344, 242; 40/2 R, 594, 395

[56] References Cited

U.S. PATENT DOCUMENTS

| | | | |
|---|---|---|---|
| 3,298,985 | 8/1983 | Eagon | 156/344 |
| 3,420,364 | 1/1969 | Kennedy, Jr. | |
| 3,531,350 | 9/1970 | Rausing et al. | 156/248 |
| 3,769,147 | 10/1973 | Komendat et al. | |
| 3,996,089 | 12/1976 | More et al. | 156/248 |
| 4,326,005 | 4/1982 | Reed et al. | 428/352 |
| 4,339,485 | 7/1982 | Shibano et al. | 428/352 |
| 4,391,853 | 7/1983 | Pointon | 428/42 |
| 4,400,419 | 8/1983 | Laczynski | 156/240 |
| 4,405,401 | 9/1983 | Stahl | 156/248 |
| 4,479,838 | 10/1984 | Dunsirn et al. | 156/247 |
| 4,544,590 | 10/1985 | Egan | 150/240 |
| 4,568,403 | 2/1986 | Egan | 156/249 |
| 4,569,857 | 2/1986 | Tung et al. | 156/249 |

OTHER PUBLICATIONS

Pressure Sensitive Tape Council, 4/1963, PSTC, Glenview, IL, 90° Peel Adhesion.

*Primary Examiner*—Robert A. Dawson
*Assistant Examiner*—Louis Falasco
*Attorney, Agent, or Firm*—Pearne, Gordon, McCoy & Granger

[57] ABSTRACT

Methods and products are disclosed in the manufacture of liner-carried "dry" tags or labels, and the manufacture of liner-carried presure-sensitive coated middle liners on which dry tags or labels are "piggybacked," and the manufacture of liner-carried coupons printable on one side. These methods and products utilize a carry-release component comprising a paper or film layer and a thermoplastic film cast or extruded onto the paper or film layer so as to be firmly but temporarily anchored thereto.

4 Claims, 2 Drawing Sheets

LABEL STOCK WITH DRY SEPARATION INTERFACE

This is a continuation of application Ser. No. 801,759, filed on Nov. 26, 1985, now abandoned.

This invention relates to non-adhesive or "dry" labels. As used herein, "labels" includes tags, coupons, identification cards and the like. Dry labels have no tack when individually handled. The invention relates particularly to liner-carried dry labels which, by high speed mass production methods, can be formed, manipulated, imprinted and, when desired, dispensed through use of a continuous supporting liner from which the labels are releasable to be ultimately separated therefrom.

BACKGROUND OF THE INVENTION

The demand for liner-carried dry labels has existed for many years, and various attempts have been made to meet this demand. These attempts have had limited success because of quality and cost problems and lack of manufacturing versatility.

One prior approach was to extrude polyethylene on facestock for a label to make up a facestock construction in which the facestock proper and the extruded polyethylene layer were permanently combined. This facestock construction, consisting of the facestock proper with its extruded polyethylene layer, was then combined with a liner construction. The liner construction consisted of a film of copolymer permanently adhered to a liner proper such as a web of paper liner. The extruded polyethylene of the facestock construction and the copolymer film of the liner construction were in contact and were intended to releasably hold the combined construction together, the interface between them being intended as the release interface of the product. When individual labels were formed, the die-cutting would, of course, extend through the facestock construction, but not through the copolymer film of the liner construction. When the individual labels or tags formed from the facestock construction were finally removed from the liner construction, they would be non-tacky or dry on both sides. This product was not reliable because the copolymer release from the polyethylene coated facestock was difficult to control. Also, manufacturing dry labels using a variety of facestocks required that each facestock be separately extrusion-coated with polyethylene. This was a costly requirement and greatly limited the variety and availability of facestocks.

Another prior art approach also formed the liner construction as a copolymer layer permanently adhered to a liner web proper. A film layer was applied over the copolymer layer in the same coating line pass in which the liner construction was formed. In a second pass, facestock was permanently adhered to the film layer to complete the facestock constructions, such facestock construction consisting of the film layer and the facestock proper adhered thereto. The interface between the film layer and the copolymer layer was intended as the release interface of the product at which the combined constructions were to be releasably held together. This product was also not reliable because the copolymer did not always provide a continuous film to completely cover the adhesive used to permanently adhere the copolymer to the liner proper. Also the product was costly because its manufacture required two passes on the coating line.

An early prior disclosure is that of Komendat and Reed U.S. Patent 3,769,147 to an assignee that is predecessor to present assignee. In this patent preformed heat softening film material 11 such as polyethylene film is laminated between a "mutable web" 10 and a base or backing 12 (FIGS. 1 and 3). The disclosure also mentions (at col. 5, line 55) coating a layer of polyethylene 26 on the backing 27 (FIG. 4) prior to lamination to the "mutable web" 31. The intention is to permanently carry the polyethylene 26 on the backing 27. Later separation occurs at the interface between elements 26 and 31.

Besides dealing with the handling and processing of "mutable webs", the Komendat and Reed patent also deals specifically with dry tags and labels, but in that instance solution-coated copolymer of vinylidene chloride and vinyl chloride (SARAN) is mentioned rather than polyethylene. The construction is shown in FIG. 6 and includes the liner or backing 63, the coating 62 of copolymer solution-coated on the backing 63, and tag stock 61 laminated to the coating 62. The tag stock is formed into tags 66 and matrix portions 68. Separation is intended to occur at the interface between the tag stock 61 and the copolymer 62. This approach is not believed to have ever come into successful use.

A still earlier prior disclosure is that of Kennedy U.S. Patent 3,420,364 assigned to Dennison Manufacturing Company. This disclosure is difficult to follow because of appararent inconsistencies (e.g. a release layer 4 is disclosed as covering a lacquer coating 3 which in turn covers a layer 2 of pressure sensitive adhesive, yet the disclosure says that the release layer should adhere to the pressure sensitive adhesive more strongly than to the lacquer) but it does reflect a prior art effort to provide liner-carried dry tag.

All of the above manufactured or disclosed products had a carry-release component shared between the facestock construction and the liner construction and consisting of the layers forming the release interface. In the first case, the carry-release component consisted of the copolymer layer and the layer of extruded polyethylene which had been laminated to the copolymer layer. In the second case, the carry-release component consisted of the copolymer layer and the film layer which had been coated on the copolymer layer. In the FIG. 6 construction of Komendat and Reed, the carry-release component consisted of the tag stock 61 and the copolymer 62 which had been coated thereon. In the Kennedy construction, the lacquer coating 3 and release material 4 seen in FIG. 2 appear to be intended to comprise a carry-release component.

THE PRESENT INVENTION

The present invention reflects the discovery that liner-carried dry label stock can novelly employ two-element "peelable papers" of specified release levels as a carry-release component forming part of the stock, such two elements comprising a paper web and a thermoplastic film extruded or cast thereon. Importantly, it has been discovered that the two elements of such carry-release components remain firmly anchored during processing steps on the combined label stock such as die-cutting, impact printing, edge perforating, and fan folding, even if such carry-release components are of a peel strength low enough to be compatible with ready and flawless removal of tags as by manual lifting. The result is a liner-carried dry label stock that is markedly superior to prior products of this kind.

Stocks for liner-carried dry label piggyback constructions may also novelly include in their constructions such carry-release components with comparable superior results.

DETAILED DESCRIPTION

By way of introduction to a description of the invention, and as will be understood by those familiar with this art, adhesive labels (wet labels) are conventionally formed and processed by several sequential operations carried on at different locations by different manufacturers (although some of such operations may be combined). The present invention provides liner-carried dry labels which meet these requirements.

Figure 1A:
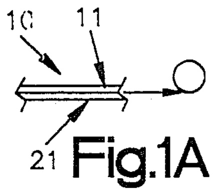
FIGS. 1A, 1B and 1C are diagrammatic illustrations of various sequences in the use of roll stock made according to the invention.

Thus, as seen in FIG. 1A, one example of the invention provides liner-carried dry label roll stock generally indicated by the reference numeral 10 and including facestock and liner constructions generally indicated by the reference numerals 11 and 21. The facestock construction is die-cut into individual labels 31 at station D seen in FIG. 1B. This step involves stripping a matrix consisting of waste portions (not shown) of the facestock construction 11. During this step the matrix of waste facestock must strip readily and cleanly from the liner construction while the portions of facestock construction that form the labels must remain firmly, but only temporarily, anchored to the liner construction.

Figure 1B:
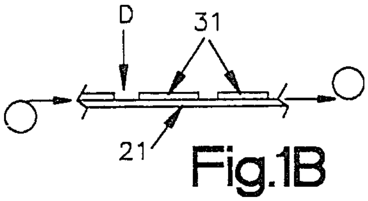
Figure 1C:
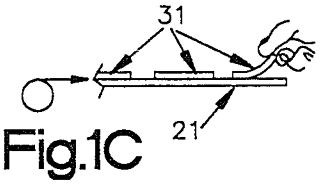

Before or after the stage illustrated in FIG. 1B, the facestock construction may be printed. Following the stage illustrated in FIG. 1B, the individual labels 31 may be readily removed from the liner construction 21 either manually as seen in FIG. 1C, or by other means. Until such removal of the individual labels, they must remain firmly, but only temporarily, anchored to the liner construction 21 during storage and shipment and during any processing steps such as printing or feeding, and also during impact printing, edge perforating and fan folding of the liner construction in applications calling for such operations, such as computer printing of labels.

Figure 2:
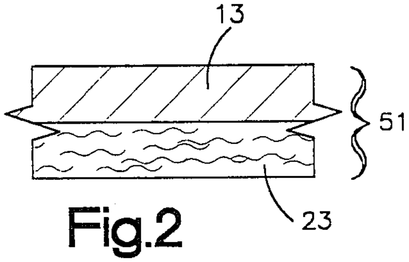
FIGS. 2-4 are fragmentary schematic cross-sections of respectively a carry-release component provided according to the invention, an intermediate product including the carry-release component, and completed label stock including the carry-release component.

According to the invention, prior to the stage seen in FIG. 1A, a carry-release component is provided consisting of a thermoplastic film cast or extruded onto a paper or film web with a peel strength at the interface between the two of 20-80 grams per inch at 90 degree peel at a peel rate of 12 inches per minute. For example, low density polyethylene 13 extruded on a web 23 of 3.1 mil bleached kraft paper and of the specified peel strength constitutes the carry-release component 51 seen in FIG. 2. "PEELABLE PAPERS" available from Schoeller Technical Papers, Inc., Pulaski, N.Y. and fabricated to the specified peel strength provide such a construction. A roll stock manufacturer then coats this construction with a pressure-sensitive adhesive 15 to provide the construction seen in FIG. 3. The roll stock manufacturer also combines the facestock proper 17 with the construction seen in FIG. 3 to provide the construction seen in FIG. 4. Or, the construction shown in FIG. 3 may be provided to a label manufacturer who, on a laminating line, adds a facestock proper 17 to provide the construction shown in FIG. 4, in which case when the construction as shown in FIG. 3 is shipped to the label manufacturer, the liner proper 23 may be coated on its outer side with a silicone release coat (not shown) and the construction may be self-wound in a well-known manner for shipment to and unwinding by the label manufacturer.

Figure 4:
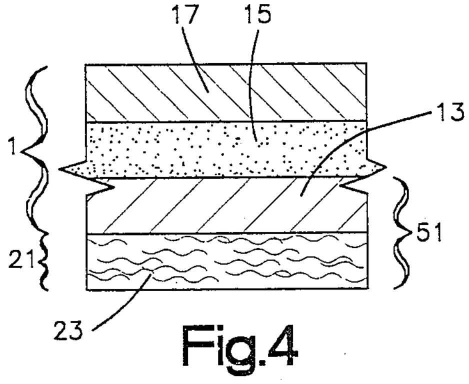

Following addition of the facestock proper 17 to produce the overall construction in FIG. 4, the facestock construction 11 now consists of the facestock proper 17, the pressure sensitive adhesive 15 and the extrusion coating of polyethylene 13. The liner construction 21 consists of the liner proper 23 to which the polyethylene 13 is firmly anchored. This is the construction included in the combination of facestock construction 11 and liner construction 21 indicated in FIGS. 1A, 1B and 1C.

Figure 3:
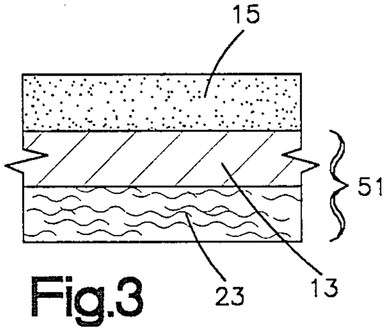

It will be understood that the manufacture of the construction of FIG. 3 will generally be done by a roll stock manufacturer. The manufacture of the construction seen in FIG. 4 will also generally be done by the roll stock manufacturer but may be done by a label manufacturer who may buy the facestock proper 17 from another source. The label manufacturer will usually perform the die-cutting operation indicated in FIG. 1B. The pick-off of individual labels as indicated in FIG. 1C will usually be done by the end user. For example, in one application the liner 21 may be fan-folded and edge perforated by the label manufacturer, and the end user may then use the stock (in fan-folded form) for computerized printing of names and addresses on dry labels or cards by the printer of a PC computer. These cards may have been die-cut in a shape that makes them usable as elements of "ROLODER" (R) type rotary card indices, and after printing the cards are simply manually picked off the fan-folded liner and inserted in the rotary indices.

Figure 5:
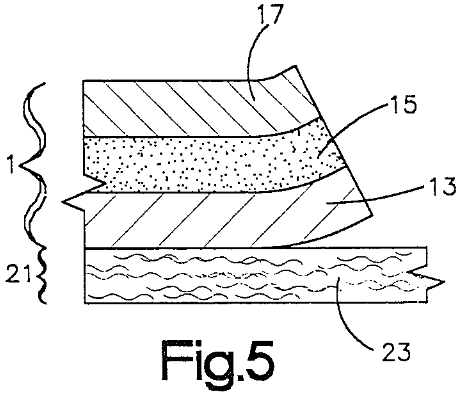
FIG. 5 illustrates a stage in the use of the product after it has been formed into individual labels.

As indicated, if a carry-release component 51 is provided according to the invention, then throughout various operations such as die-cutting offset or impact printing, edge perforating, fan-folding, shipping and handling, and storage, the labels 31 remain firmly anchored to the liner construction but, at the proper time, can be stripped from the liner in a flawless and controlled manner by lifting the labels from the liner construction, or peeling back the liner construction, to separate the layers 13 and 23 as indicated in FIG. 5.

Figure 6:
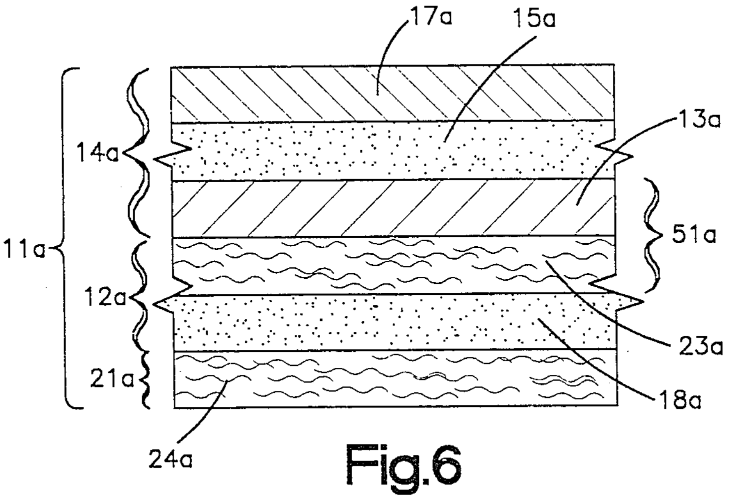
FIG. 6 illustrates another form of the invention in which a carry-release component made according to the invention is used in a piggyback label.

The invention may be used to provide dry base "piggyback" in which dry-based labels are carried or piggybacked on a pressure-sensitive coated liner construction. Such a construction is shown in FIG. 6. In this case a construction similar to FIG. 4 is provided comprising low density polyethylene 13*a* extruded on web 23*a*. However the web 23*a* of FIG. 6 is not the bottom liner as is the web 23 of FIGS. 2–4. Rather, the web 23*a* is the liner proper of a middle pressure-sensitive coated liner construction 12*a* comprising the web 23*a* and a layer 18*a* of pressure sensitive adhesive. A liner construction 21*a* consists of a liner proper 24*a* with a silicone release coat (not shown) on its adhesive side. The facestock proper 17*a* and pressure sensitive adhesive 15*a* together with the extruded polyethylene layer 13*a* constitute the dry facestock construction 14*a*. The middle liner construction 12*a* and dry facestock construction 14*a* together constitute an overall piggyback label construction 11*a*. In this embodiment the carry-release component 51*a*, comprising the web 23*a* with the layer 13*a* extruded thereon, is shared between the facestock and middle liner constructions 14*a* and 12*a* of the overall piggyback label construction 11*a*.

It will be seen that if the layers 13*a*, 15*a*, 17*a* and 23*a* of FIG. 6 are identical to layers 13, 15, 17 and 23 of FIG. 4, then the construction of FIG. 6 represents simply the addition of the adhesive layer 18*a* and liner proper 24*a* to the simpler construction. However the layer 23 of FIG. 4 is the only liner proper while the layer 23*a* of FIG. 6 is the liner proper of the middle liner construction, so it may be desirable to choose different material for layer 23*a* than say a 3.1 mil bleached kraft paper mentioned above as a suitable material for the layer 23. However in both instances the layers 23 and 23*a* constitute a carrier layer which supports and carries the polyethylene layers 13 and 13*a* and the other higher layers constituting the dry facestock construction portion of each product.

The stock of FIG. 6 may be processed somewhat similarly to that of FIG. 4 in a manner that would be illustrated in FIGS. 1A, 1B and 1C if the reference numerals 11*a* and 21*a* were substituted for 11 and 21. Thus the overall piggyback label construction 11*a* and liner construction 21*a* may be manufactured in roll form by a roll stock manufacturer in a manner similr to that suggested for this facestock construction 11 and liner construction 21 of FIG. 1A. This product can be shipped to a label manufacturer who then, before or after printing the facestock, die-cuts the product into individual labels in a manner similar to that suggested in FIG. 1B, the die-cuts extending of course through the overall piggyback label construction 11*a* but not through the liner construction 21*a*. The printed liner-supported labels may then be rolled in the manner indicated in FIG. 1*b*, or may be stacked in sheet form, for storage and shipment to a packager of manufactured products or some other user.

Figure 6A:
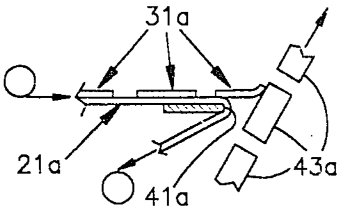
FIG. 6A is a view similar to FIG. 1C illustrating application of the piggyback label of FIG. 6.

Individual labels 31*a* (FIG. 6A) cut from the overall piggyback label construction 11*a* are carried on the liner construction 21*a* until peeled therefrom by a conventional industrial applicator device utilizing a peelback edge, or by other means, to expose the pressure sensitive adhesive 18*a* and apply the label 31*a* to one of a series of passing workpieces 43*a* on a packaging line or the like in the manner illustrated in FIG. 6A (in which a peelback edge 41*a* is shown). Or, the individual labels 31*a* are removed from the liner construction 21*a* and applied manually or by other means. Peeling occurs at the facestock between the liner proper 24*a* and the layer 18*a* of pressure sensitive adhesive, the carry-release component 51*a* remaining if desired in its "carry" mode during the first peel due to the firmness of the temporary anchoring provided even at peel strengths of about 20–80 grams per inch width at 12 inches per minute peel rate. When the now-exposed pressure-sensitive adhesive 18*a* is applied against the mounting surface (not shown), the label is held firmly to that surface. At this point the label consists of the piggybacked construction, the middle liner construction 12*a* being supported by the mounting surface and the dry facestock construction 14*a* being supported in piggyback relationship on the liner construction 12*a*. The dry facestock construction 14*a* remains temporarily but firmly anchored in place during additional handling, say during additional handling of packaged goods through retail channels of trade, but can readily be removed in a flawless and controlled manner when desired, say by a consumer when the dry facestock construction 14*a* constitutes a return coupon.

Figure 7:
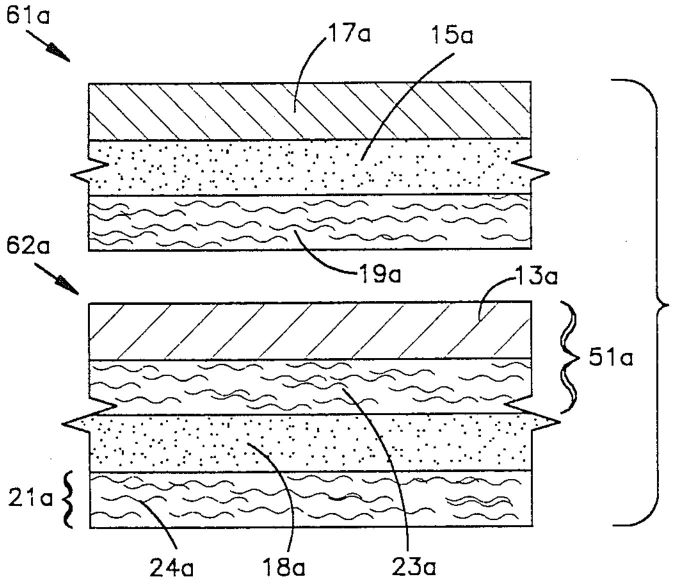
FIG. 7 illustrates an alternative which allows printing on both sides of the dry labels formed from the roll stock.

The roll stock manufacturer may supply two components as shown in FIG. 7. Here the elements are generally similar to those of the FIG. 6 construction. However the product is supplied by the roll stock manufacturer as two components, 61*a* and 62*a*. Component 61*a* includes not only facestock proper 17*a* and pressure sensitive adhesive 15*a* but also liner 19*a* coated on the adhesive side with a silicone release coat (not shown.) Component 62*a* includes the polyethylene layer 13*a*, the web 23*a* (which together with the polyethylene layer makes up the carry-release component 51*a*), the pressure-sensitive adhesive layer 18*a*, and the liner proper 24*a*.

The label manufacturer removes the liner 19*a* and laminates the remainder of component 61*a* to component 62*a* to form the construction of FIG. 6. Before doing so however, the label manufacturer may print the top surface of the polyethylene layer 13*a* while that surface is still exposed. Since the polyethylene is transparent, this printing will show on the underside of the ultimately separated dry label. The surface of the facestock proper 17*a* may of course be printed before or after the laminating step, or even after the die-cutting of individual tags or labels. The product that results from these steps is a liner-carried roll or sheet of a series of carriers cut from the pressure-sensitive coated middle liner construction 12*a* and on each of which is piggybacked a dry tag or label printed on both sides.

The liner-carried label shown being removed in FIG. 5 may be referred to as "dry base" in the sense that the label, i.e., the facestock construction 11, includes not only the facestock proper 17 but also the facestock "base" comprising the adhesive 15 and the polyethylene layer 13. In contrast, the invention also contemplates provision of a product in which the facestock construction consists of a single layer or facestock proper. A description of such a product follows.

Figure 8:
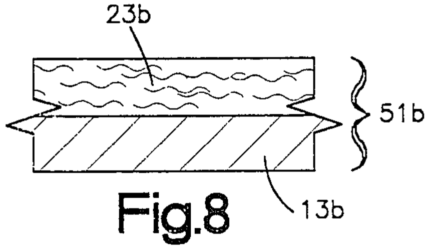
FIGS. 8-10 illustrate another form of the invention and show respectively a carry-release component, a completed label stock including the carry-release component, and a stage in the use of the product after it has been die-cut into individual labels.
Figure 9:
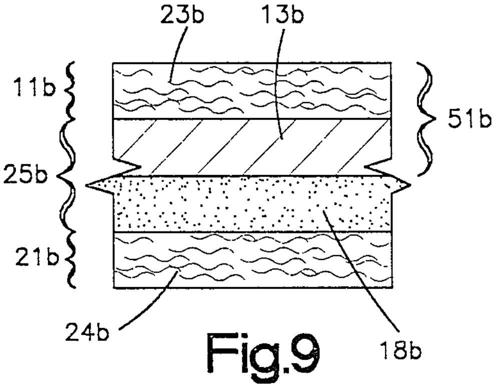

Shown in FIG. 8 is a thermoplastic film 13*b* which has been extruded onto paper or film facestock proper 23*b*. Together these layers make up the carry-release component 51*b*. These layers are combined with the adhesive layer 18*b* and liner proper 24*b* which is provided on the adhesive side with a release coat (not shown). The entire liner construction 21*b* consists of the liner proper 24*b* and its release coat. In this roll stock, a "base" construction 25*b* is located between the facestock construction 11*b* and the liner construction 21*b*.

Figure 10:
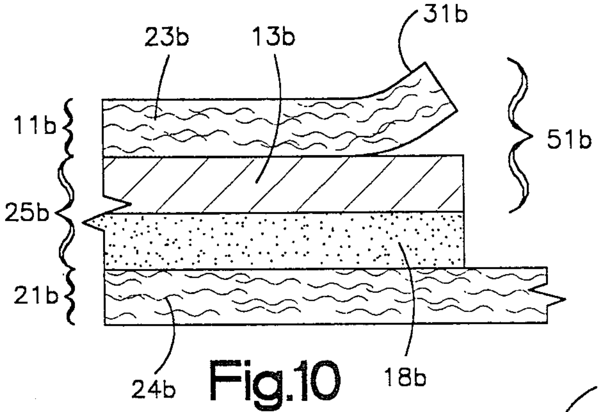

Roll stock in this form can be supplied to a label manufacturer who prints and die-cuts individual labels such as the coupon 31*b* (FIG. 10) each supported on its own die-cut portion of the base construction 25*b*, the die-cuts in this case extending to but not through the liner construction 21*b*. The die-cut labels can then be shipped to, say, a packager to be dispensed and applied to passing packages in a manner similar to that illustrated in FIG. 6A in connection with the piggyback construction. The consumer or end user can then manually pick off an individual coupon 31*b* by raising one end as shown in FIG. 10 and peeling. Until this time the coupon remains firmly anchored to its base which in turn is firmly anchored to the package or other substrate by the pressure-sensitive adhesive 18*b*.

Figure 11:
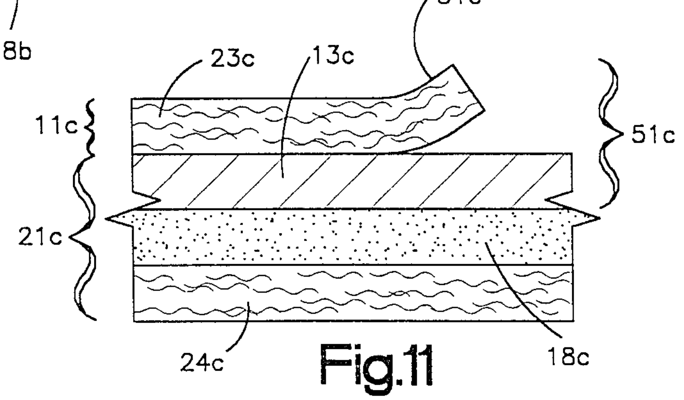
FIG. 11 is a view similar to FIG. 10 showing still another form of the invention.

In another product shown in FIG. 11, a thermoplastic film 13*c* has been extruded onto a paper or film facestock proper 23*c*, the layers together making up the carry-release component 51*c*. These layers are combined with the adhesive layer 18*c* and the liner proper 24*c*. However, the liner proper 24*c* is not provided with a release coat, and the layers 13*c*, 18*c* and 24*c* remain permanently combined into the liner construction 21*c*. The facestock construction 11*c* consists solely of the paper or film facestock proper 23*c*. The label manufacturer die-cuts only through the facestock construction 11*c*. This roll stock product may be used to produce sheets or rolls of liner-carried printed labels which are manually picked off by an end user in a manner similar to that illustrated in FIG. 1C in connection with the first described embodiment of the invention.

It will be understood that each of the liners proper 23, 24*a*, 24*b* and 24*c* are primary since they support all other elements of the respective products described. It will also be understood that in all the products described above there is a face side (top side in the drawings) and liner side (bottom side in the drawings). In all of them there is a carry-release component 51, 51*a*, 51*b* or 51*c* whose two layers define between them a separation interface. In all these products, the one of these two layers that is on the liner side of the separation interface (layers 23, 23*a*, 13*b* or 13*c*) is a carrier layer that supports all elements that are on the face side of the separation interface, including at least the other of the two layers (13, 13*a*, 23*b* or 23*c*) of the carry-release component. All these products include a primary liner proper (23, 24*a*, 24*b*, 24*c*) which either is comprised of the carrier layer (23) or is adhered to the carrier layer (24*a* is adhered to 23*a*, 24*b* is adhered to 13*b*, 24*c* is adhered to 13*c*).

It should be evident that this disclosure is by way of example and that various changes may be made by adding, modifying or eliminating details without departing from the fair scope of the teaching contained in this disclosure. The invention is therefore not limited to particular details of this disclosure except to the extent that the following claims are necessarily so limited.

What is claimed is:

1. An article of manufacture comprising a roll or sheet stock for liner-carried labels, said stock having elements that form a face side and a liner side and including a separately formed carry-release component, said carry-release component including two layers, a first of said two carry-release layers being a preformed paper or film layer, a second of said two carry-release layers being a layer of thermoplastic film cast or extruded directly onto said first carry-release layer and anchored thereto without an intermediate adhesive layer at a dry separation interface therebetween, said carry-release component providing a peel strength at said separation interface of about 20–80 grams per inch width at 90° peel and a peel rate of 12 inches per minute, either of said two carry-release layers being a carrier layer which is on a liner side of said separation interface and which supports any of said elements that is on a face side of said separation interface, said stock including a pressure-sensitive adhesive in contact with one of said carry-release layers as the result of mutual contact therebetween subsequent to the formation of the carry-release component, the separately formed carry-release component being characterized by a mechanical strength and inerfacial peel strength sufficient to enable it to be self-supporting and to permit it to be machine assembled with said pressure-sensitive adhesive, said stock further including another layer adhesively assembly to said one carry-release layer by said pressure-sensitive adhesive, the adherence of said pressure-sensitive adhesive to said one carry-release layer being greater than the peel strength of anchoring between said two carry-release layers at said dry separaation interface, the peel strength of anchoring between said two carry-release layers at said separation interface being sufficiently high to sustain forces occurring when the adhesively assembled stock is die cut into individual labels from a face side thereof at least through the carry-release layer other than the carrier layer at least to said separation interface and through an additional one of said layers while being sufficiently low to permit subsequent stripping of such die cut labels from said carrier layer.

2. An intermediate article of manufacture comprising the roll or sheet stock of claim 1 having at least one continuous layer on the liner side of said interface and being die cut and stripped from the face side thereof at least to said interface but not through said continuous layer to form a succession of spaced labels each firmly but temporarily anchored to said carrier layer.

3. An article of manufacture comprising a roll or sheet stock for liner-carried labels having a face side and a liner side and including a separately formed carry-release component, a label layer directly or indirectly assembled to the face side of said carry-release component by a pressure-sensitive adhesive, said carry-release component including a first of two layers which is a preformed paper or film layer and a second of two layers which is a layer of thermoplastic film cast or extruded directly onto said first layer and anchored thereto without an intermediate adhesive layer at a dry separation interface therebetween with a peel strength at said separation interface of about 20–80 grams per inch width at 90 degrees peel and a peel rate of 12 inches per minute, said pressure-sensitive adhesive being in contact with one of said carry-release layers on the face side of the dry separation interface, the carry-release component being characterized by a mechanical strength and interfacial peel strength sufficient to enable it to be self-supporting and to permit it to be machine assembled with said pressure-sensitive adhesive, the adherence of said pressure-sensitive adhesive to said one carry-release layer being greater than the peel strength of anchoring between said two carry-release layers at said dry separation interface, either of said two carry-release layers being a carrier layer which is on a liner side of said separation interface and which supports all of the layers that are on a face side of said separation interface, a peel strength of anchoring between said two carry-release layers at said separation interface being sufficiently high to sustain forces occurring when the stock is die cut into individual labels from a face side thereof at least through the carry-release layer other than the carrier layer to said separation interface while being sufficiently low to permit subsequent stripping of such die cut labels from said carrier layer.

4. An intermediate article of manufacture comprising the roll or sheet stock of claim 3 having at least one continuous layer on the liner side of said interface and being die cut and stripped from the face side thereof at least to said interface but not through said continuous layer to form a succession of spaced labels each firmly but temporarily anchored to said carrier layer.

* * * * *